US005177254A

United States Patent [19]

Haji et al.

[11] Patent Number: 5,177,254

[45] Date of Patent: Jan. 5, 1993

[54] METHOD FOR PRODUCING AN UNSATURATED GLYCOL DIESTER

[75] Inventors: Junzo Haji, Yokohama; Ichiro Yokotake, Yokohama; Takahiro Yamaguchi, Yokohama; Masato Sato, Yokohama; Nobuyuki Murai, Yokkaichi, all of Japan

[73] Assignee: Mitsubishi Chemical Industries Limited, Tokyo, Japan

[21] Appl. No.: 152,339

[22] Filed: Feb. 4, 1988

[30] Foreign Application Priority Data

Apr. 23, 1987 [JP] Japan ........................ 62-100844

[51] Int. Cl.[5] .................... C07C 67/05

[52] U.S. Cl. .................... 560/244

[58] Field of Search .................... 560/244

[56] References Cited

U.S. PATENT DOCUMENTS 3,755,423 8/1973 Onoda et al. .................... 560/244
3,922,300 11/1975 Onoda et al. .................... 560/244
4,075,413 2/1978 Tanabe et al. .................... 560/244
4,122,285 10/1978 Weitz et al. .................... 560/244

FOREIGN PATENT DOCUMENTS 2424539 12/1974 Fed. Rep. of Germany .
2100778 11/1977 Fed. Rep. of Germany .
2726125 12/1977 Fed. Rep. of Germany .

*Primary Examiner*—Jose G. Dees
*Assistant Examiner*—Joseph M. Conrad
*Attorney, Agent, or Firm*—Oblon, Spivak, McClelland, Maier & Neustadt

[57] ABSTRACT

A method for producing an unsaturated glycol diester by reacting molecular oxygen, a carboxylic acid and a conjugated diene in the presence of a solid catalyst containing palladium and tellurium supported on a carrier, wherein an active carbon with the total pore volume of pores having radii of from 18 to 100,000 Å being at least 0.45 cc/g and with the volume of pores having radii of at least 3,000 Å constituting at least 50% of the total pore volume, is used as the carrier for the solid catalyst.

7 Claims, No Drawings

METHOD FOR PRODUCING AN UNSATURATED GLYCOL DIESTER

The present invention relates to a method for producing an unsaturated glycol diester from a conjugated diene. More particularly, it relates to a method for producing a butenediol diester from butadiene.

A Butenediol diester is an important intermediate compound for 1,4-butanediol as a starting material for engineering plastics, elastomers, elastic fibers, synthetic leathers, etc. or for tetrahydrofuran as a starting material for high performance solvents or elastic fibers.

Heretofore, a number of proposals have been reported with respect to methods for the production of a butenediol diester. Among them, a method for producing a butenediol diester by reacting butadiene with a carboxylic acid and molecular oxygen by means of a solid catalyst having palladium and tellurium supported on active carbon is well known. Japanese Examined Patent Publication No. 29727/1977 proposes a method for producing a butenediol diester advantageously by using a pulverized coconut shell active carbon pretreated with nitric acid, as a carrier for a solid catalyst for the reaction.

Further, Japanese Unexamined Patent Publication No. 146289/1979 proposes a method for producing a butenediol diester advantageously by further improving the activating method of the catalyst by using a pulverized coconut shell active carbon treated with nitric acid.

However, neither method was fully satisfactory although they had a feature that a butenediol diester can thereby be produced more advantageously than by other conventional methods, and it was thereby difficult to provide a catalyst having higher catalytic activities and a less tendency for deterioration of the catalytic activities.

It is an object of the present invention to overcome the above-mentioned problems and to provide a catalyst having high catalytic activities and a minimum tendency for deterioration of the catalytic activities, which is thus useful as a catalyst for producing a butenediol diester from the molecular oxygen, butadiene and a carboxylic acid advantageously on an industrial scale.

The present inventors have conducted extensive research on the influence of the catalyst carrier over the catalytic properties with an aim to solve the conventional problems and as a result, have found it possible to obtain a catalyst having higher catalytic activities and a less tendency for deterioration of the activities by using an active carbon carrier having a certain specific structure. The present invention has been accomplished on the basis of this discovery.

The present invention provides a method for producing an unsaturated glycol diester by reacting molecular oxygen, a carboxylic acid and a conjugated diene in the presence of a solid catalyst containing palladium and tellurium supported on a carrier, wherein an active carbon with the total pore volume of pores having radii of from 18 to 100,000 Å being at least 0.45 cc/g and with the volume of pores having radii of at least 3,000 Å constituting at least 50% of the total pore volume, is used as the carrier for the solid catalyst.

Now, the present invention will be described in detail with reference to the preferred embodiments.

The carrier for a solid catalyst used in the method of the present invention is active carbon, particularly an active carbon having a special structure.

Namely, as measured by a mercury porosimeter based on the following fundamental relation of the pore radius and the pressure in a porous structure measurement:

$$Pr = -2\Psi \cos\theta$$

where P is the pressure, r is the pore radius, $\Psi$ is the surface tension of mercury and $\theta$ is the contact angle between the mercury and the sample, under the measuring conditions of $\Psi = 480$ dyne/cm and $\theta = 140°$, the active carbon has a special structure such that the total pore volume of pores having radii of from 18 to 100,000 Å is at least 0.45 cc/g and the volume of pores having radii of at least 3,000 Å constitutes at least 50% of the total pore volume (such active carbon being referred to hereinafter as a "special structure active carbon").

Active carbons are generally classified into plant carbon and mineral carbon depending upon their sources, and it is well known that the respective carbons have their own physical properties and chemical properties.

The active carbon useful in the present invention may be plant carbon or mineral carbon, or a mixture of both, so long as it is an active carbon having the above-mentioned special structure.

A preferred porous structure for the special structure active carbon is such that the total pore volume is at least 0.45 cc/g and the volume of pores having radii of at least 3,000 Å constitutes at least 55% of the total pore volume. A more preferred porous structure of the special structure active carbon is such that the total pore volume is at least 0.55 cc/g and the volume of pores having radii of at least 3,000 Å is at least 55% of the total pore volume.

There is no particular restriction as to the shape of the special structure active carbon, and it may be in any form such as a powder form, a pulverized form, a granular form, a columnar form, etc. Likewise, there is no particular restriction as to the particle size of the active carbon to be used. In the case of a granular carbon, however, the particle size is usually from 1.0 to 4.0 mm. Likewise, in the case of a carbon of a cylindrical shape, the diameter is usually from 1.0 to 4.0 mm.

The active carbon having the special structure of the present invention can be selected from active carbons commercially available for use in the food industry or in the adsorption treatment.

A commercial product of the special structure active carbon may be used by itself as a carrier for a solid catalyst, thereby to obtain a catalyst carrier having high activities and a small tendency for the deterioration of the activities. However, it is preferred to pretreat it with nitric acid by a method as disclosed in Japanese Examined Patent Publication No. 29726/1977, thereby to obtain a catalyst carrier having higher activities and a less tendency for deterioration of the activities.

Well known methods for the preparation of metal catalysts supported on carriers may suitably be employed to have the catalyst components supported on the special structure active carbon. For example, a palladium compound and a tellurium compound may be dissolved in an aqueous nitric acid solution, and the special structure active carbon is added to the solution, whereupon the above components will be adsorbed and supported on the carrier. Then, the metal catalyst supported on the carrier is collected by filtration and reduced in a stream of hydrogen or an organic compound having reducing power, or in a liquid phase by means of a reducing agent such as hydrazine or formalin.

The palladium compound to be used for the preparation of the catalyst is preferably palladium nitrate. However, other palladium compounds such as palladium chloride and palladium acetate may, of course, be used. There is no particular restriction as to the palladium compound. If desired, palladium metal may be used. The concentration of palladium supported on the carrier may be varied within a wide range of from 0.1 to 20% by weight. However, usually it is preferred to be within a range of from 0.5 to 10% by weight.

The tellurium compound to be used for the preparation of the catalyst may be a halide such as tellurium (II) chloride or tellurium (IV) chloride, an oxide such as tellurium (IV) oxide or tellurium (VI) oxide, telluric acid or tellurium metal.

The concentration of tellurium supported on the carrier may be varied within a wide range. It is usually preferred that the concentration is within a range of from 0.01 to 30% by weight. The ratio of tellurium to palladium in the catalyst is usually preferably within a range of from 0.01 to 10 g atom relative to 1 g atom of palladium, more preferably from 0.05 to 5 g atom relative to 1 g atom of palladium.

The conjugated diene to be used as the starting material in the method of the present invention may not necessarily be pure and may contain an inert gas such as nitrogen or a saturated hydrocarbon such as methane, ethane or butane.

The carboxylic acid as another starting material may be a lower aliphatic monocarboxylic acid such as acetic acid, propionic acid or butyric acid. Acetic acid is particularly preferred from the viewpoint of the reactivity and low costs.

In addition to the above carboxylic acid, an organic solvent inert to the reaction, such as a hydrocarbon or an ester, may be present in the reaction medium. However, at least 50% by weight of the reaction medium should preferably be the carboxylic acid starting material. The carboxylic acid is used in an amount within a range of from the stoichiometric amount to 60 mols relative to 1 mol of conjugated diene.

The molecular oxygen may not necessarily be pure oxygen and may be oxygen diluted with an inert gas such as nitrogen, such as air. There is no particular restriction as to the amount of the oxygen to be used. It may be used within a range wherein the supplied gas will not have an explosive composition.

The reaction of the molecular oxygen, conjugated diene and the carboxylic acid in the presence of the solid catalyst according to the method of the present invention may be conducted in an optional system such as a fixed bed system, a fluidized bed system or a suspended catalyst system.

The reaction is conducted usually at a temperature of at least 20° C. A preferred range of the reaction temperature is from 60° to 180° C. when the reaction rate and the production of by-products are taken into accounts. There is no particular restriction as to the reaction pressure. The reaction is usually conducted under atmospheric pressure or under a pressure of a few atm. It is, of course, possible to conduct the reaction under a higher pressure.

Now, the method of the present invention will be described in further detail with reference to the Examples. However, it should be understood that the present invention is by no means restricted by such specific Examples.

EXAMPLE 1

30 g of water and 30 g of a 60 wt % nitric acid aqueous solution were added to 20 g of a special structure active carbon (coal type) having a diameter of 3 mm and a length of 6 mm wherein the total pore volume of pores having radii of from 18 to 100,000 Å was 0.59 cc/g and the volume of pores having radii of at least 3,000 Å0 constituted 59.7% of the total pore volume. The mixture was maintained at a temperature of from 90° to 94° C. for 3 hours. After cooling the mixture, the solution was removed by filtration to obtain a special structure active carbon treated with nitric acid. Then, 60 g of an aqueous solution obtained by dissolving palladium nitrate and tellurium metal was added thereto, and the mixture was maintained at 30° C. for 3 hours, and then left to cool for 5 hours. Then, the solution was removed again by filtration, and the mixture was dried under a pressure of 240 torr at a maximum temperature of 140° C. to obtain a palladium and tellurium-supported special structure active carbon (hereinafter referred to simply as a "supported catalyst") containing 3.6% by weight of palladium and 0.65% by weight of tellurium.

Of the above supported catalyst, 30 cc was packed (height of the packed layer: 6 cm) in a Pyrex glass activating container having an inner diameter of 2.5 cm (effective cross-sectional area: 4.9 $c^2$). While supplying nitrogen containing 8% by volume of methanol gas at a flow rate of 39 Nl/hr, the temperature was raised at a rate of 50° C./hr. When the temperature reached 400° C., the system was maintained under the same condition for 4 hours and then left to cool to room temperature under a nitrogen stream. Then, the supply gas was changed to nitrogen containing 2% by volume of oxygen gas, and while supplying such nitrogen at a flow rate of 39 Nl/hr, the system was maintained at 300° C. for 15 hours and then left to cool under a nitrogen stream. Again, while supplying nitrogen containing 8% by volume of methanol gas at a flow rate of 39 Nl/hr, the temperature was raised at a rate of 50° C./hr. When the temperature reached 400° C., the system was maintained for 15 hours and then cooled to room temperature under a nitrogen stream. Then, while supplying nitrogen containing 2% by volume of oxygen gas at a rate of 39 Nl/hr, the system was maintained at 300° C. for 1 hour and then cooled under a nitrogen stream.

Then, while supplying hydrogen gas at a flow rate of 39 Nl/hr instead of the nitrogen gas containing 8% by volume of methanol gas, the temperature was raised at a rate of 50° C.,/hr. When the temperature reached 400° C., the system was maintained for 4 hours and then left to cool in a nitrogen stream. Then, while supplying nitrogen containing 2% by volume of oxygen at a rate of 39 Nl/hr, the system was maintained at 300° C. for 15 hours and then cooled in a nitrogen stream. Then, the above reducing treatment with hydrogen gas was repeated to complete the activating treatment of the supported catalyst. This activation-treated supported catalyst (hereinafter referred to as an "activated catalyst") contained 4.0% by weight of palladium and 0.72% by weight of tellurium.

Then, 4 g of this activated catalyst was packed in a stainless steel reaction tube having an inner diameter of 12 mm (effective cross-sectional area: 0.848 $cm^2$), and 0.122 mol/hr of 1,3-butadiene, 2.5 mol/hr of acetic acid and 96.4 Nl/hr of nitrogen containing 6% by volume of oxygen were supplied and continuously reacted for 4,000 hours under a reaction pressure of 60 kg/$cm^2$ at a reaction temperature of 80° C.

Upon expiration of a prescribed period of time after the initiation of the reaction, the formed solution was analyzed to obtain the amount of diacetoxybutene produced per hour per g of the activated catalyst. The results are shown in Table 1.

COMPARATIVE EXAMPLE 1

The operation was conducted in the same manner as in Example 1 except that a pulverized coconut shell active carbon of from 4 to 6 mesh wherein the total pore volume (hereinafter referred to simply as "A") of pores having radii of from 18 to 100,000 Å was 0.34 cc/g and the volume (hereinafter referred to simply as "B") of pores having radii of at least 3,000 Å constituted 42.1% of the total pore volume, was used as the carrier for the catalyst in the process of Example 1. The results are shown in Table 1.

EXAMPLE 2

The operation was conducted in the same manner as in Example 1 except that a special structure active carbon having a diameter of 3 mm and a length of 6 mm wherein A was 0.45 cc/g and B was 50%, was used as the carrier for the catalyst and the reaction was conducted continuously for 500 hours in the process of Example 1. The results are shown in Table 2.

EXAMPLE 3

The operation was conducted in the same manner as in Example 2, except that a special structure active carbon having a diameter of 3 mm and a length of 6 mm wherein A was 0.45 cc/g and B was 55%, was used as the carrier for the catalyst in the process of Example 2. The results are shown in Table 2.

COMPARATIVE EXAMPLE 2

The operation was conducted in the same manner as in Example 2 except that a shaped coconut shell active carbon having a diameter of 3 mm and a length of 6 mm wherein A was 0.38 cc/g and B was 58.7%, was used as the carrier for the catalyst in the process of Example 1. The results are shown in Table 2.

COMPARATIVE EXAMPLE 3

The operation was conducted in the same manner AS IN Example 2 except that a shaped brown coal active carbon having a diameter of 3 mm and a length of 6 mm wherein A was 0.46 cc/g and B was 35.0%, was used as the carrier for the catalyst in the process of Example 1. The results are shown in Table 2.

TABLE 1

| Type of carrier | Porous structure *1) A (cc/g) | *2) B (%) | Reaction time (hr) | *3) Products (mmol/g. cat. hr) 3,4-diacetoxybutene-1 | 1,4-diacetoxybutene-2 |
|---|---|---|---|---|---|
| Example 1 | | | | | |
| Special structure | 0.59 | 59.7 | 100 | 0.62 | 6.7 |
| active carbon | | | 300 | 0.51 | 5.5 |
| (3 mmφ × 6 mmL) | | | 500 | 0.46 | 4.9 |
| | | | 1,000 | 0.38 | 4.1 |
| | | | 2,000 | 0.33 | 3.6 |
| | | | 4,000 | 0.32 | 3.4 |
| Comparative Example 1 | | | | | |
| Pulverized | 0.34 | 42.1 | 100 | 0.59 | 5.5 |
| coconut shell | | | 300 | 0.44 | 4.1 |
| active carbon | | | 500 | 0.37 | 3.5 |
| (4-6 mesh) | | | 1,000 | 0.29 | 2.7 |
| | | | 2,000 | 0.20 | 1.9 |
| | | | 4,000 | 0.15 | 1.4 |

1) Total volume of pores having radii of from 18 to 100,000 Å

2) Proportion of the volume of pores having radii of at least 3,000 Å relative to the total pore volume.

3) Amount of the product produced per hour per g of the activated catalyst.

TABLE 2

| Type of carrier | Porous structure A (cc/g) | B (%) | Reaction time (hr) | Products (mmol/g. cat. hr) 3,4-diacetoxybutene-1 | 1,4-diacetoxybutene-2 |
|---|---|---|---|---|---|
| Example 2 | | | | | |
| Special structure | 0.45 | 50.0 | 100 | 0.53 | 5.8 |
| active carbon | | | 300 | 0.44 | 4.7 |
| | | | 500 | 0.40 | 4.3 |
| Example 3 | | | | | |
| Special structure | 0.45 | 55.0 | 100 | 0.58 | 6.2 |
| active carbon | | | 300 | 0.45 | 4.9 |
| | | | 500 | 0.41 | 4.4 |
| Comparative Example 2 | | | | | |
| Shaped coconut | 0.38 | 58.7 | 100 | 0.60 | 5.7 |
| shell active | | | 300 | 0.45 | 4.2 |
| carbon | | | 500 | 0.38 | 3.6 |
| (3 mmφ × 6 mmL) | | | | | |
| Comparative Example 3 | | | | | |
| Shaped brown coal | 0.46 | 35.0 | 100 | 0.34 | 3.2 |
| active carbon | | | 300 | 0.29 | 2.7 |
| (3 mmφ × 6 mmL) | | | 500 | 0.24 | 2.2 |

As described in detail in the foregoing, it is possible to obtain a catalyst having a higher activity and a less tendency for deterioration of the activity by using the special structure active carbon as the carrier of a solid catalyst. Thus, the industrial significance of the present invention is substantial.

We claim:

1. A method for producing an unsaturated glycol diester by reacting molecular oxygen, a carboxylic acid and a conjugated diene in the presence of a solid catalyst containing palladium and tellurium supported on a carrier, wherein an active carbon with the total pore volume of pores having radii of from 18 to 100,000 Å being at least 0.45 cc/g and with the volume of pores having radii of at least 3,000 Å constituting at least 50% of the total pore volume, is used as the carrier for the solid catalyst.

2. The method according to claim 1, wherein in the active carbon, the volume of pores having radii of at least 3,000 Å constitutes at least 55% of the total pore volume.

3. The method according to claim 1, wherein in the active carbon, the total volume of pores having radii of from 18 to 100,000 Å is at least 0.55 cc/g and the volume of pores having radii of at least 3,000 Å constitutes at least 55% of the total pore volume.

4. The method according to claim 1, wherein the concentration of palladium supported on the active carbon is from 0.1 to 20% by weight.

5. The method according to claim 1, wherein the concentration of tellurium supported on the active carbon is from 0.01 to 30% by weight.

6. The method according to claim 1, wherein the g atom ratio of tellurium to palladium supported on the active carbon is Te/Pd=0.01 to 10.

7. The method according to claim 1, wherein said carboxylic acid is acetic acid and said conjugated diene is butadiene.

* * * * *

UNITED STATES PATENT AND TRADEMARK OFFICE
CERTIFICATE OF CORRECTION

PATENT NO. : 5,177,254

DATED : January 5, 1993

INVENTOR(S) : Junzo Haji et al.

It is certified that error appears in the above-identified patent and that said Letters Patent is hereby corrected as shown below:

On the title page, Item [73],

The assignee's information is incorrect, should read as follows:

--Mitsubishi Kasei Corporation, Tokyo, Japan--

Signed and Sealed this

First Day of March, 1994

*Attest:*

BRUCE LEHMAN

*Attesting Officer*

*Commissioner of Patents and Trademarks*